(12) United States Patent
Airaksinen et al.

(10) Patent No.: US 9,585,580 B2
(45) Date of Patent: Mar. 7, 2017

(54) METHOD AND APPARATUS FOR DETERMINING INFORMATION INDICATIVE OF CARDIAC MALFUNCTIONS AND ABNORMALITIES

(71) Applicant: TURUN YLIOPISTO, Turun yliopisto (FI)

(72) Inventors: Juhani Airaksinen, Turku (FI); Tero Koivisto, Turku (FI); Joona Marku, Turku (FI); Ari Paasio, Littoinen (FI); Mikko Pankaala, Raisio (FI); Kati Sairanen, Naantali (FI); Tuomas Valtonen, Turku (FI); Peter Virta, Turku (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 0 days.

(21) Appl. No.: 14/396,204

(22) PCT Filed: Apr. 17, 2013

(86) PCT No.: PCT/FI2013/050421
§ 371 (c)(1),
(2) Date: Oct. 22, 2014

(87) PCT Pub. No.: WO2013/160537
PCT Pub. Date: Oct. 31, 2013

(65) Prior Publication Data
US 2015/0133806 A1    May 14, 2015

(30) Foreign Application Priority Data
Apr. 23, 2012    (FI) ..................................... 20125442

(51) Int. Cl.
*A61B 5/04* (2006.01)
*A61B 5/00* (2006.01)
(Continued)

(52) U.S. Cl.
CPC .......... *A61B 5/04012* (2013.01); *A61B 5/046* (2013.01); *A61B 5/0456* (2013.01);
(Continued)

(58) Field of Classification Search
CPC .......................... A61B 5/04012; A61B 5/0452
See application file for complete search history.

(56) References Cited

U.S. PATENT DOCUMENTS 8,251,911 B2    8/2012  MacQuarrie et al.
9,427,176 B2    8/2016  Skerl et al.
(Continued)

FOREIGN PATENT DOCUMENTS

CN    1088075    6/1994
CN    101801263    8/2010
(Continued)

OTHER PUBLICATIONS

Inan O T et al.: "Robust ballistocardiogram acquisition for home monitoring", Physiological Measurement, Institute of Physics Publishing, Bristol, GB, vol. 30, No. 2, Feb. 1, 2009 (Feb. 1, 2009), pp. 169-185, XP020153654, ISSN: 0967-3334, 001: 10.1088/0967-3334/30/2/005 p. 172, line 1—p. 173, line 22 p. 179, line 1—p. 181, line 21 table 1 figures 4,5.

(Continued)

*Primary Examiner* — Eric D. Bertram
(74) *Attorney, Agent, or Firm* — Young & Thompson

(57) ABSTRACT

An apparatus for determining information indicative of cardiac malfunctions and abnormalities includes a processing device (402) configured to extract, from a signal indicative of electromagnetic phenomena related to cardiac activity, a first wave pattern repeating on a heart-beat rate and, from a signal indicative of cardiovascular motion, a second wave pattern repeating on the heart-beat rate. The processing device is configured to form timing data such that each (Continued)

timing value of the timing data is indicative of a time period from a reference point of the first wave pattern belonging to one heart-beat period to a reference point of the second wave pattern belonging to the same heart-beat period. The processing device is configured to determine, at least partly on the basis of the timing data, an indicator of cardiac malfunction and abnormality.

33 Claims, 6 Drawing Sheets

(51) Int. Cl.
    *A61B 5/0452* (2006.01)
    *A61B 5/0456* (2006.01)
    *A61B 5/046* (2006.01)
    *A61B 5/11* (2006.01)

(52) U.S. Cl.
    CPC ........ *A61B 5/04525* (2013.01); *A61B 5/1102* (2013.01); *A61B 5/7246* (2013.01); *A61B 5/7275* (2013.01)

(56) References Cited

U.S. PATENT DOCUMENTS

| | | | |
|---|---|---|---|
| 2002/0103442 A1* | 8/2002 | Mulligan | A61B 5/0215 600/513 |
| 2003/0233034 A1 | 12/2003 | Varri et al. | |
| 2006/0293605 A1 | 12/2006 | Zanetti et al. | |
| 2008/0194975 A1 | 8/2008 | Macquarrie et al. | |
| 2009/0163815 A1 | 6/2009 | Kawagishi et al. | |
| 2010/0210921 A1 | 8/2010 | Park et al. | |
| 2011/0130671 A1 | 6/2011 | Macquarrie et al. | |

FOREIGN PATENT DOCUMENTS

| | | |
|---|---|---|
| EP | 1 747 752 A1 | 1/2007 |
| EP | 2433565 A1 | 3/2012 |
| JP | 2004-538035 A | 12/2004 |
| WO | 92/20284 A1 | 11/1992 |
| WO | 02/43584 A2 | 6/2002 |
| WO | 2005/011475 A2 | 2/2005 |
| WO | 2011/068687 A1 | 6/2011 |
| WO | 2012/149652 A1 | 5/2012 |

OTHER PUBLICATIONS

Wick C. A., et al, A trimodal system for the acquisition of synchronous echocardiography, electrocardiography, and seismocardiography data, 33rd Annual International Conference of the IEEE Engineering in Medicine and Biology Society, 30.08.2011, Conference Proceeding Article, pp. 6911-6914 <doi:1 0.11 09/IEMBS.2011.6091740> x abstract; section IV Conclusion.

International Search Report, dated Jul. 22, 2013, from corresponding PCT application.

FI Search Report, dated Dec. 18, 2012, from corresponding FI application.

CN Office Action, dated Nov. 27, 2015; Application No. 201380021430.5.

Japanese Office Action, dated Nov. 29, 2016, from corresponding Japanese Patent Application No. JP 2015-507565.

Da He, David, Eric S. Winokur, and Charles G. Sodini. "A continuous, wearable, and wireless heart monitor using head ballistocardiogram (BCG) and head electrocardiogram (ECG)." Engineering in Medicine and Biology Society, EMBC, 2011 Annual International Conference of the IEEE. pp. 4729-4732. IEEE, 2011.

* cited by examiner

METHOD AND APPARATUS FOR DETERMINING INFORMATION INDICATIVE OF CARDIAC MALFUNCTIONS AND ABNORMALITIES

FIELD OF THE INVENTION

The invention relates generally to determining information indicative of cardiac malfunctions and abnormalities, such as for example atrial fibrillation. More particularly, the invention relates to an apparatus and to a method for determining information indicative of cardiac malfunctions and abnormalities. Furthermore, the invention relates to a computer program for determining information indicative of cardiac malfunctions and abnormalities.

BACKGROUND

Malfunctions and abnormalities that may occur in the cardiovascular system, if not diagnosed and appropriately treated or remedied, may progressively decrease the ability of the cardiovascular system to supply, inter alia, sufficient oxygen to satisfy the coronary oxygen demand when the individual encounters stress. Currently, methods such as cardiography based on electromagnetic phenomena related to cardiac activity, echocardiography, and cardiography based on cardiovascular motion are used in the identification and assessment of various cardiac malfunctions and abnormalities. A well-known example of the cardiography based on electromagnetic phenomena related to cardiac activity is the electrocardiography "ECG", and examples of the cardiography based on cardiovascular motion are ballistocardiography "BCG" and seismocardiography "SCG". The echocardiography provides images of sections of the heart and can provide comprehensive information about the structure and function of the heart, but requires expensive equipment and specialised operating personnel. The ECG provides a fairly rapid electrical assessment of the heart, but does not provide any information relating to forces of contraction. The cardiography based on cardiovascular motion involves measurement of a signal indicative of cardiovascular motion. Earlier, the signal was obtained while an individual lay on a bed that was provided with an apparatus for measuring movements or there was a facilitating apparatus that was attached across the shin area of the legs. Currently, the signal can be obtained using small sensor elements, e.g. accelerometers, which are suitable for measuring minute movements which are representative of movements of the heart.

FIGS. 1a and 1b show the relationship between rhythmic electrical functions and related cardiovascular motions. FIG. 1a shows an example of an ECG waveform and FIG. 1b shows a waveform of an exemplifying signal indicative of cardiovascular motion and measured with an accelerometer in the "head-to-foot"-direction that is typically referred to as the y-direction. For the sake of illustrative purposes, a brief explanation of basic heart functions is provided below.

The heart includes four chambers. The right atrium is interconnected with the right ventricle by the tricuspid valve, and the left atrium is interconnected with the left ventricle by the mitral valve. Blood is delivered to the right atrium from the upper half of the body via the superior vena cava, and from the lower half of the body via the inferior vena cava. The tricuspid valve is opened by concurrent contraction of the right atrium myocardium and the right ventricular papillary muscles thereby allowing blood flow from the right atrium into the right ventricle. Then the tricuspid valve closes when the papillary muscles relax. When the myocardium of the right ventricle contracts, blood is forced from the right ventricle through the pulmonary valve into the pulmonary artery which delivers the blood into the lungs wherein it is oxygenated. The oxygenated blood is then delivered to the left atrium via pulmonary veins. The oxygenated blood flows from the left atrium into the left ventricle when the mitral valve is opened by concurrent contraction of the left atrium myocardium and the left ventricular papillary muscles thereby allowing blood flow from the left atrium into the left ventricle. Then the mitral valve is closed when the papillary muscles relax. The oxygenated blood is then forced out from the left ventricle through the aortic valve into the aorta which delivers the oxygenated blood to the peripheral vascular system.

Each heart-beat period involves three major stages: the atrial systole, the ventricular systole and the cardiac diastole. The atrial systole is the period of contraction of the heart muscles encompassing the right and left atria. Both atria contract concurrently with the papillary muscle contraction thereby forcing open the tricuspid valve and the mitral valve. The electrical activity, i.e. the electrical systole, which stimulates the muscle tissue of the chambers of the heart to make them contract begins in the sinoatrial node located in the right atrium. The conduction electrical depolarization continues to travel as a wave downwards, leftwards, and posteriorly through both atria depolarising each atrial muscle cell in turn. This propagation of charge can be seen as the P-wave on the ECG waveform shown in FIG. 1a. This is closely followed by mechanical contraction of the atria that is detected as an impact which corresponds to the h-peak of the waveform shown in FIG. 1b and to a recoil which corresponds to the i-valley of the waveform shown in FIG. 1b. When the right and left atria begin to contract, there is a high velocity flow of blood into the right and left ventricles, which is represented by the j-peak on the waveform shown in FIG. 1b. The continuing atrial contraction, when the tricuspid valve begins to close, causes an additional lower velocity flow of blood into the right and left ventricles. The additional flow of blood is called the "atrial kick", which corresponds to the "a-a$^1$"-wave complex in the waveform shown in FIG. 1b. After the atria are emptied, the tricuspid and mitral valves close thereby giving rise to the downward g-wave on the waveform shown in FIG. 1b. The ventricular systole is the contraction of the muscles of the left and right ventricles, and is caused by the electrical depolarization of the ventricular myocardia giving rise to the "Q-R-S"-wave complex in the ECG waveform shown in FIG. 1a. The downward Q-wave is caused by the downward flow of depolarisation through the septum along a specialized group of cells called "the bundle of His". The R-peak is caused by depolarization of the ventricular muscle tissue, and the S-wave is produced by depolarization of the heart tissue between the atria and ventricles. As the depolarization travels down the septum and throughout the ventricular myocardia, the atria and sinoatrial node start to polarise. The closing of the tricuspid and mitral valves mark the beginning of ventricular systole and cause the first part of the "lub-dub" sound made by the heart as it beats. This sound is typically known as the "first heart tone". When the electrical depolarization of the ventricular myocardia peaks, the atrioventricular "AV" septum separating the right and left ventricles contracts causing an impact, which corresponds to the H-peak on the waveform shown in FIG. 1b, and a recoil which corresponds to the I-valley on the waveform shown in FIG. 1b. The ventricular contraction forces the blood from the right ventricle into the pulmonary artery through the pulmonary valve, and from the left ventricle into the aorta through the aortic valve under very high velocity thereby causing the J-peak on the waveform shown in FIG. 1b. The deceleration of blood flow from the left ventricle into the aorta causes the downward K-wave on the waveform shown in FIG. 1b. When the left ventricle empties, its pressure falls below the pressure in the aorta and the aortic valve closes. Similarly, when the pressure in the right ventricle falls below the pressure in the pulmonary artery, the pulmonary valve closes. The second part of the "lub-dub" sound, which is typically known as the "second heart tone", is caused by the closure of the pulmonary and aortic valves at the end of ventricular systole thereby causing the upward L-wave on the waveform shown in FIG. 1b. Concurrently with the closing of the pulmonary and aortic valves, the atrioventricular "AV" septum relaxes and moves upward, and the ventricular myocardia is re-polarized giving rise to the T-wave on the ECG waveform shown in FIG. 1a. The cardiac diastole, which includes the atrial diastole and the ventricular diastole, is the period when the heart relaxes after contraction and prepares for being refilled with circulating blood. Atrial diastole is when the right and left atria are relaxing, and the ventricular diastole is when the right and left ventricles are relaxing. During the period of the atrial diastole, the right atrium is re-filled by deoxygenated blood while the left atrium is re-filled with oxygenated blood. Re-filling of the atria causes the downward M-wave on the waveform shown in FIG. 1b early in the diastole which coincides with repolarization of the bundle of His cells, which is shown as the U-wave in the ECG waveform. When the right and left atria are filled to their maximum capacities, the reflux of blood against the tricuspid valve and mitral valve cause the upward N-wave on the waveform shown in FIG. 1b.

Publication WO2012149652 describes a method for assessment of cardiac contractility in a subject by recording precordial acceleration signals.

Publication US2008194975 describes a method for monitoring an individual's physiological condition and detecting abnormalities therein. The method comprises concurrently receiving a first signal that is an ECG signal and a second signal indicative of cardiovascular motion.

Analysis of waveforms indicative of cardiovascular motion is typically performed visually by qualified diagnosticians in order to distinguish abnormal cardiovascular function from normal cases. In many cases, however, it may be challenging to find out certain cardiac malfunctions and abnormalities, such as for example atrial fibrillation, by visual analysis. Thus, a need exists for methods and apparatuses for determining information indicative of cardiac malfunctions and abnormalities.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new method for determining information indicative of cardiac malfunctions and abnormalities, e.g. atrial fibrillation. The method according to the invention comprises:

extracting, from a first signal indicative of electromagnetic phenomena related to cardiac activity, a first wave pattern repeating on a heart-beat rate, extracting, from a second signal indicative of cardiovascular motion, a second wave pattern repeating on the heart-beat rate, forming timing data, each timing value of which being indicative of a time period from a reference point of the first wave pattern belonging to one heart-beat period to a reference point of the second wave pattern belonging to the same heart-beat period, and determining correlation between the timing data and pacing data indicative of the heart-beat rate, the correlation being indicative of cardiac malfunction and abnormality.

The second wave pattern is advantageously selected to be such that it represents a response of the heart to the first wave pattern on the first signal. The first signal can represent, for example, an electrocardiograph "ECG" waveform or an inductively measured waveform. The first wave pattern can be, for example but not necessarily, the R-peak of the "Q-R-S"-wave complex on the ECG waveform shown in FIG. 1a, and the second wave pattern can be, for example but not necessarily, the J-peak on the waveform shown in FIG. 1b. In this case, the top of the R-peak can be used as the reference point of the first wave pattern and the top of the J-peak can be used as the reference point of the second wave pattern, and each timing value can indicate the time period from the moment of the top of the R-peak to the moment of the top of the J-peak. For another example, the second wave pattern can be the aortic valve opening "AO"-peak on a waveform indicative of cardiovascular motion measured in the "through chest"-direction that is typically referred to as the z-direction.

The method may further comprise detecting the above-mentioned pacing data from the first signal indicative of electromagnetic phenomena related to cardiac activity and/or from the second signal indicative of cardiovascular motion. The detection of the pacing data may comprise, for example, detecting time periods between successive R-peaks of an ECG waveform. It is also possible that the pacing data indicative of the heart-beat rate is formed on the basis of a third signal measured from individual's body.

The above-mentioned correlation between the timing data and the pacing data can be used as the indicator of cardiac malfunction and abnormality. For example, in light of empirical data, a positive correlation means an increased probability of atrial fibrillation when each value of the pacing data represents an instantaneous value of the heart-beat rate, e.g. in beats per minute. Correspondingly, when each value of the pacing data represents a temporal length of one heart-beat period e.g. in seconds, i.e. 1/heart-beat rate, a negative correlation means an increased probability of atrial fibrillation.

The degree of the correlation between the timing data and the pacing data can be expressed, for example but not necessarily, with the aid of a correlation coefficient that can be computed according to the following equation:

$$C(j)=E\{(TD-\mu_T)\times(PD-\mu_P)\},$$

where $C(j)$ is the correlation coefficient, $E$ is the expected value operator, i.e. $E\{variable\}$ is the expected value of the variable, TD is the timing data, $\mu_T$ is the mean of the timing data, PD is the pacing data, $\mu_P$ is the mean of the pacing data, and j is an integer expressing a time-lag of the pacing data with respect to the timing data in heart-beat periods. In light of empirical results, it is advantageous that the pacing data PD has a lag of one heart-beat period with respect to the timing data TD, i.e. j=1. In this case, when the timing data TD relates to a given heart-beat period, the corresponding pacing data PD relates to the previous heart-beat period. The correlation coefficient can be expressed in a form $\rho_{T,P}$ that it is always on the range from −1 to +1:

$$\rho_{T,P}=C(j)/(\sigma_T \times \sigma_P),$$

where $\sigma_T$ and $\sigma_P$ are the standard deviations of the timing data and the pacing data, respectively.

It is to be noted that there are numerous ways for expressing the possible correlation between the timing data and the pacing data, and the present invention is not limited to any particular way of expressing the correlation. Furthermore, it is to be noted that the correlation is not necessarily a mathematical quantity but it refers to any of a broad class of statistical relationships involving dependence, and that the correlation in its general sense does not imply or require causation.

In a method according to another exemplifying embodiment of the invention, the determining of the indicator of cardiac malfunction and abnormality comprises determining variation of the timing data at a substantially constant heart-beat rate. For example, in light of empirical data, the standard deviation of the timing data can be about 10% of the mean value during atrial fibrillation and about 1-2% of the mean value in a normal case.

A method according to an exemplifying embodiment of the invention comprises low-pass filtering a signal indicative of cardiovascular motion and detecting the above-mentioned AO-peaks from the low-pass filtered signal and/or band-pass filtering the signal indicative of the cardiovascular motion and detecting AC-peaks from the band-pass filtered signal, where the AC-peaks are caused by the closures of the aortic valve. The upper limit frequency of the low-pass filtering can be, for example but not necessarily, 30 Hz, and the pass-band of the band-pass filtering can be, for example but not necessarily, from 40 Hz to 100 Hz. The low-pass filtering and/or the pass-band filtering facilitate the detection of the AO- and/or AC-peaks. Especially during atrial fibrillation, the AC-peaks are easier to find when the band-pass filtering is used than when there is no band-pass filtering. The detected AO- and/or AC-peaks can be utilized when extracting for example the above-mentioned second wave pattern from the signal indicative of cardiovascular motion. The detected AO- and/or AC-peaks can be used for many other purposes too, e.g. for detecting an amplitude variation, a time variation, the heart-beat rate, the systolic intervals, and/or the diastolic intervals.

In accordance with the invention, there is provided also a new apparatus for determining information indicative of cardiac malfunctions and abnormalities. The apparatus according to the invention comprises:
  a signal interface for receiving a first signal indicative of electromagnetic phenomena related to cardiac activity and a second signal indicative of cardiovascular motion,
  a processing device coupled to the signal interface and configured to:
  a) extract from the first signal a first wave pattern repeating on a heart-beat rate and from the second signal a second wave pattern repeating on the heart-beat rate,
  b) form timing data, each timing value of which being indicative of a time period from a reference point of the first wave pattern belonging to one heart-beat period to a reference point of the second wave pattern belonging to the same heart-beat period, and
  c) determine correlation between the timing data and pacing data indicative of the heart-beat rate, the correlation being indicative of cardiac malfunction and abnormality.

The apparatus may further comprise a first sensor element for measuring the first signal indicative of electromagnetic phenomena related to cardiac activity and/or a second sensor element for measuring the second signal indicative of cardiovascular motion. The first sensor element may comprise electrodes suitable for being attached to individual's body. The second sensor element may comprise, for example, an accelerometer, a piezo-electronic sensor, an inclinometer, a pressure sensor, or any other element suitable for measuring force, acceleration, displacement, or any other quantity related to and indicative of cardiovascular motion. It is also possible that the signal interface is capable of receiving the first signal and/or the second signal from an external device comprising appropriate sensor elements, i.e. it is emphasized that the apparatus does not necessarily comprise means for measuring the first signal and/or the second signal.

An apparatus according to an exemplifying embodiment of the invention comprises a low-pass filter for low-pass filtering a signal indicative of the cardiovascular motion and means, e.g. a processor, for detecting the AO-peaks from the low-pass filtered signal and/or a band-pass filter for band-pass filtering the signal indicative of the cardiovascular motion and means for detecting the AC-peaks from the band-pass filtered signal.

In accordance with the invention, there is provided also a new computer program for determining information indicative of cardiac malfunctions and abnormalities. The computer program comprises computer executable instructions for controlling a programmable processor to:
  extract, from a first signal indicative of electromagnetic phenomena related to cardiac activity, a first wave pattern repeating on a heart-beat rate,
  extract, from a second signal indicative of cardiovascular motion, a second wave pattern repeating on the heart-beat rate,
  form timing data, each timing value of which being indicative of a time period from a reference point of the first wave pattern belonging to one heart-beat period to a reference point of the second wave pattern belonging to the same heart-beat period, and
  determine correlation between the timing data and pacing data indicative of the heart-beat rate, the correlation being indicative of cardiac malfunction and abnormality.

A computer program according to an exemplifying embodiment of the invention comprises computer executable instructions for controlling a programmable processor to low-pass filter a signal indicative of the cardiovascular motion and to detect the AO-peaks from the low-pass filtered signal and/or computer executable instructions for controlling the programmable processor to band-pass filter the signal indicative of the cardiovascular motion and to detect the AC-peaks from the band-pass filtered signal.

In accordance with the invention, there is provided also a new computer program product. The computer program product comprises a non-volatile computer readable medium, e.g. a compact disc "CD", encoded with a computer program according to the invention.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of also un-recited features. The features recited in depending claims are mutually freely combinable unless otherwise explicitly stated.

BRIEF DESCRIPTION OF THE FIGURES

The exemplifying embodiments of the invention and their advantages are explained in greater detail below with reference to the accompanying drawings, in which:

FIGS. 1a and 1b have already been explained when describing the background of the invention.

DESCRIPTION OF THE EXEMPLIFYING EMBODIMENTS

Figure 1A:
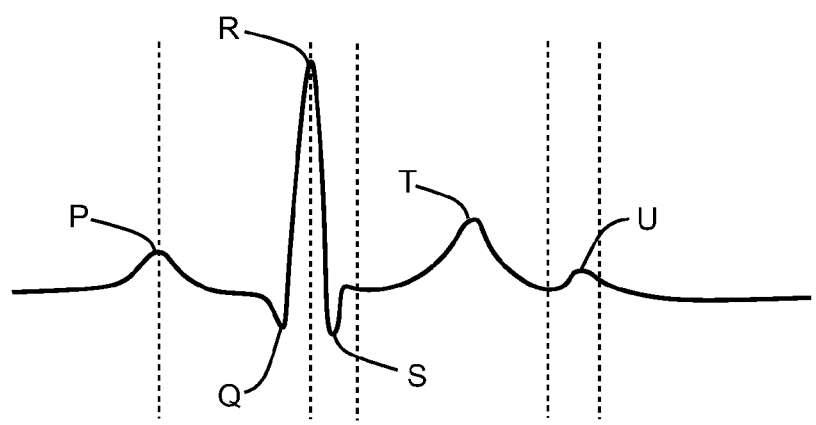
FIG. 1a illustrates an example of an ECG waveform and FIG. 1b illustrates a waveform of an exemplifying signal indicative of cardiovascular motion and measured with an accelerometer in the "head-to-foot"-direction that is typically referred to as the y-direction.
Figure 1B:
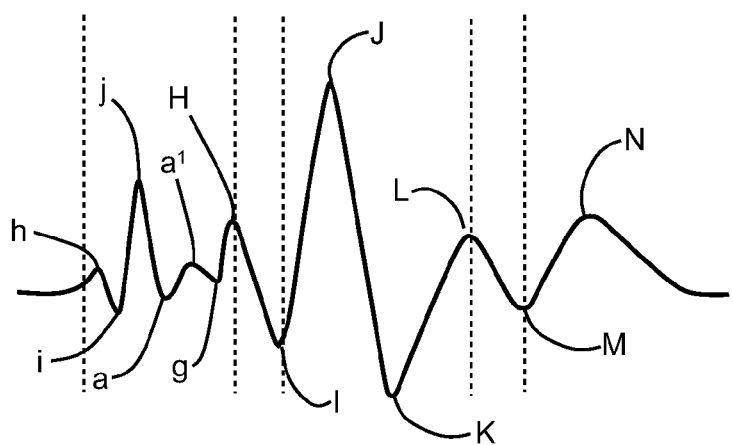
Figure 2A:
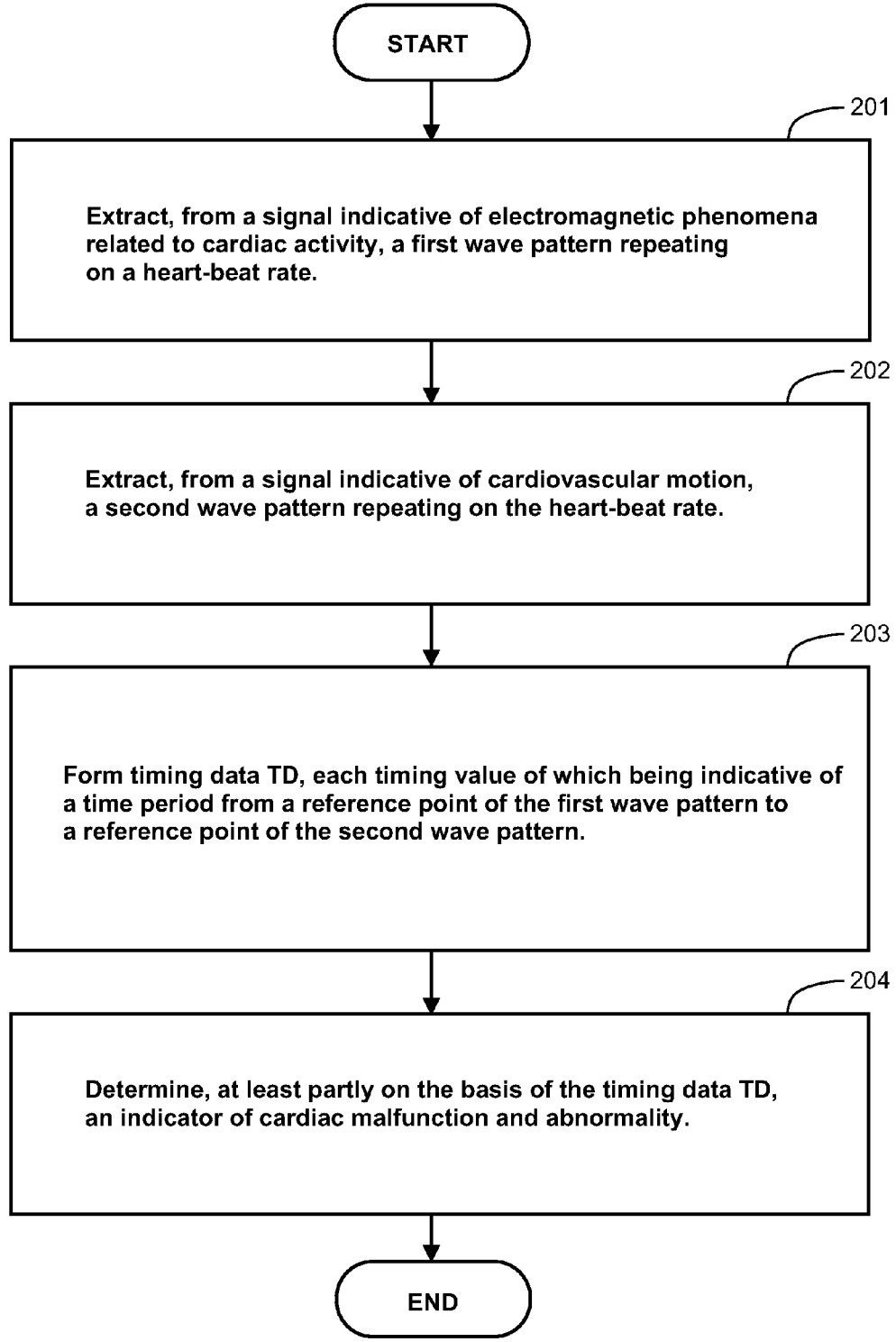
FIG. 2a illustrates a flow chart of a method according to an exemplifying embodiment of the invention for determining information indicative of cardiac malfunctions and abnormalities.

FIG. 2a illustrates a flow chart of a method according to an exemplifying embodiment of the invention for determining information indicative of cardiac malfunctions and abnormalities, e.g. atrial fibrillation. The method comprises in a phase 201 extracting, from a first signal indicative of electromagnetic phenomena related to cardiac activity, a first wave pattern repeating on a heart-beat rate. The method comprises in a phase 202 extracting, from a second signal indicative of cardiovascular motion, a second wave pattern repeating on the heart-beat rate. The first and second signals are/have been measured simultaneously from a same individual. The method comprises in a phase 203 forming timing data TD such that each timing value of the timing data is indicative of a time period from a reference point of the first wave pattern belonging to one heart-beat period to a reference point of the second wave pattern belonging to the same heart-beat period. The method comprises in a phase 204 determining, at least partly on the basis of the timing data TD, an indicator of cardiac malfunction and abnormality.

Figure 3A:
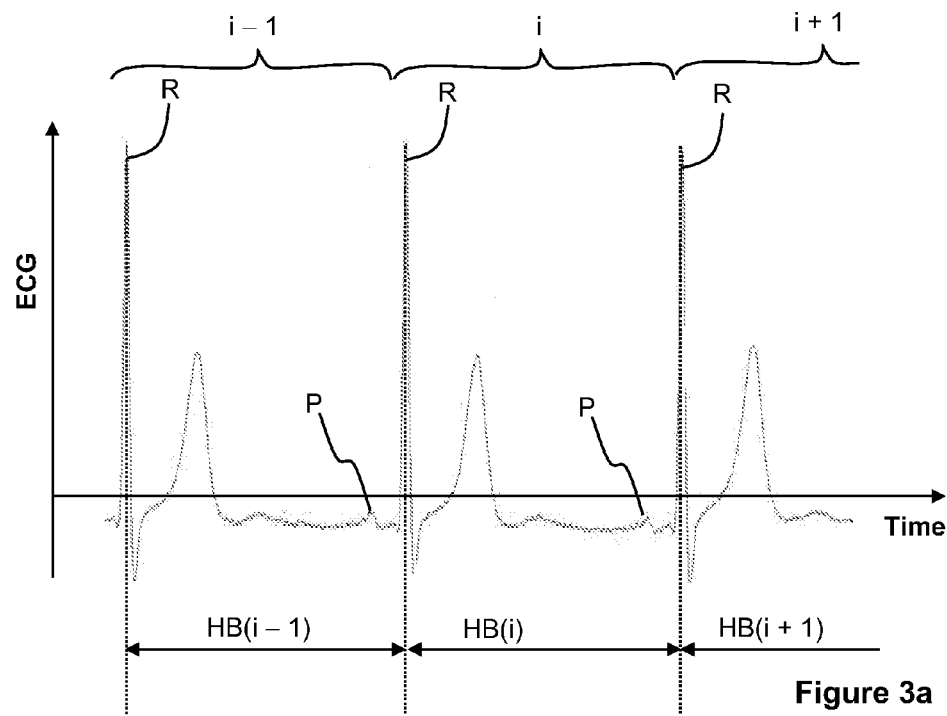
FIG. 3a illustrates an exemplifying ECG waveform and FIG. 3b illustrates a waveform of an exemplifying signal indicative of cardiovascular motion and measured with an accelerometer in the "through chest"-direction that is typically referred to as the z-direction.
Figure 3B:
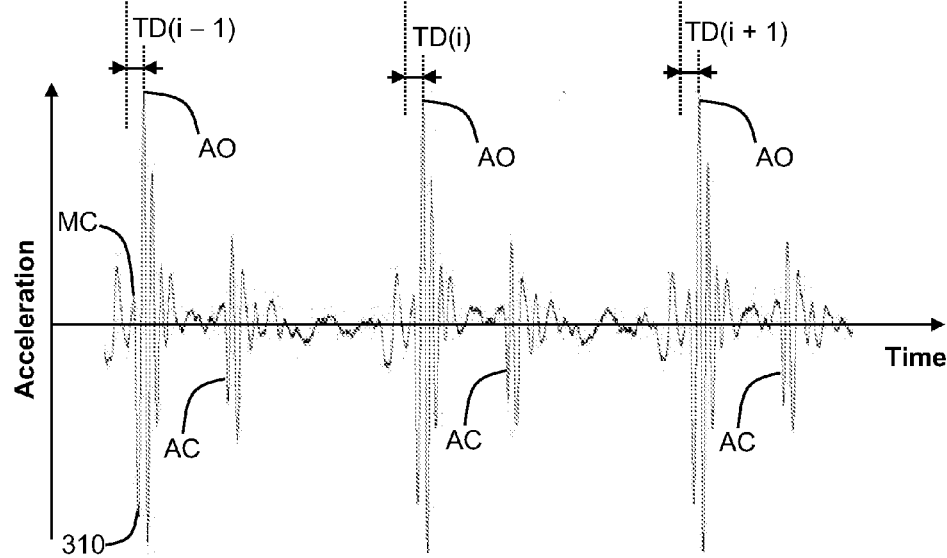
Figure 4:
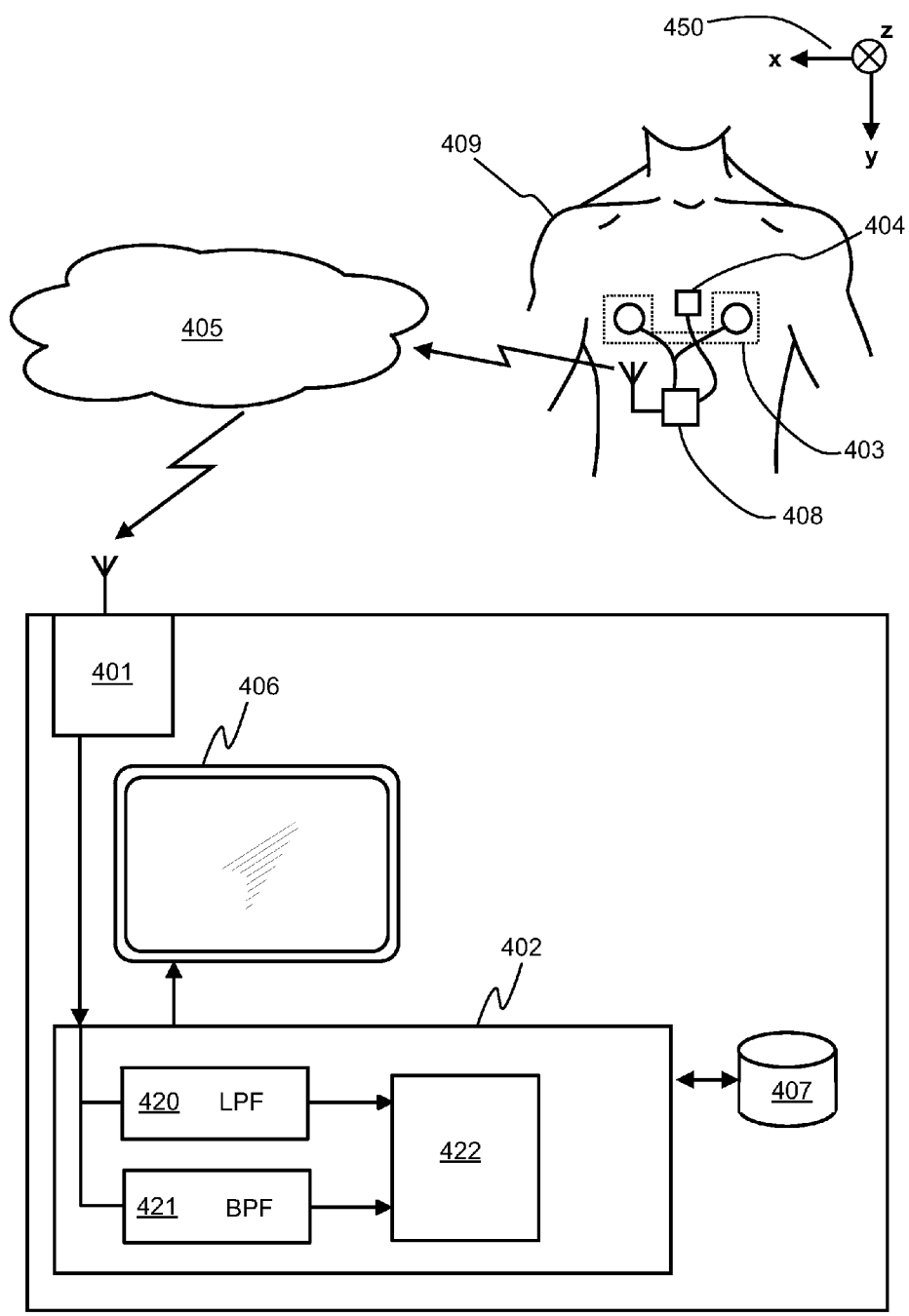
FIG. 4 shows a schematic illustration of an apparatus according to an exemplifying embodiment of the invention for determining information indicative of cardiac malfunctions and abnormalities.

FIG. 3a illustrates a waveform of an exemplifying signal indicative of electromagnetic phenomena related to cardiac activity, and FIG. 3b illustrates a waveform of an exemplifying signal indicative of cardiovascular motion. The waveforms shown in FIGS. 3a and 3b correspond to each other so that they have been measured simultaneously from a same individual. The waveform shown in FIG. 3a is an ECG waveform that has been measured with the aid of electrodes attached to the individual's chest, and the waveform shown in FIG. 3b has been measured with an accelerometer in the "through chest"-direction that is typically referred to as the z-direction. A coordinate system 450 shown in FIG. 4 illustrates the z-direction.

FIGS. 3a and 3b together illustrate an exemplifying way to define the timing data TD. In this exemplifying case, the R-peak appearing on the ECG waveform and caused by depolarization of the ventricular muscle tissue represents the first wave pattern repeating on the heart-beat rate, and the aortic valve opening "AO"-peak of the waveform indicative of cardiovascular motion represents the second wave pattern repeating on the heart-beat rate. The top of the R-peak is the reference point of the first wave pattern and the top of the AO-peak is the reference point of the second wave pattern.

In a method according to another exemplifying embodiment of the invention, the R-peak represents the first wave pattern and the J-peak appearing on a waveform measured in the head-to-foot direction and caused by blood flow from the left ventricle into the aorta through the aortic valve represents the second wave pattern. The top of the R-peak can be used as the reference point of the first wave pattern and the top of the J-peak can be used as the reference point of the second wave pattern.

In a method according to one exemplifying embodiment of the invention, the R-peak represents the first wave pattern and the valley 310 between the MC-peak and the AO-peak appearing on the waveform shown in FIG. 3b represents the second wave pattern. The MC-peak is caused by closure of the mitral valve. The top of the R-peak can be used as the reference point of the first wave pattern and the deepest point of the valley 310 can be used as the reference point of the second wave pattern.

FIGS. 3a and 3b illustrate three successive heart-beat periods: the heart-beat period "i−1", the heart-beat period "i", and the heart-beat period "i+1" where "i" can be an integer. For example, the timing value TD(i) related to the heart-beat period "i" is the time period from the moment of the top of the R-peak of the heart-beat period "i" to the moment of the top of the J-peak of the heart-beat period "i" as illustrated by FIGS. 3a and 3b.

The action 204 shown in FIG. 2a comprises determining correlation between the timing data TD and pacing data PD that is indicative of the heart-beat rate. In light of empirical results, the correlation can be used as the indicator of cardiac malfunction and abnormality.

The method may further comprise detecting the pacing data PD indicative of the heart-beat rate from the waveform indicative of electromagnetic phenomena related to cardiac activity and/or from the waveform indicative of cardiovascular motion. The detection of the pacing data may comprise, for example, detection of time periods between successive R-peaks on an ECG waveform. It is also possible that the detection of the pacing data comprises, for example, detection of time periods between successive AO- or J-peaks on a waveform indicative of cardiovascular motion. It is possible to utilize more than one waveform in order to get more reliable pacing data. Furthermore, it is also possible that a third signal is measured from individual's body, and this third signal alone or together with the waveform indicative of electromagnetic phenomena related to cardiac activity and/or the waveform indicative of cardiovascular motion is used for determining the pacing data indicative of the heart-beat rate. In FIG. 3a, the temporal lengths of the time periods between the successive R-peaks are denoted with HB(i−1), HB(i), and HB(i+1). The pacing data for the heart-beat periods "i−1", "i", and "i+1" can be defined, for example, as PD(i−1)=1/HB(i−1), PD(i)=1/HB(i), and PD(i+1)=1/HB(i+1), respectively.

The correlation between the timing data TD and the pacing data PD can be expressed with the aid of a mathematical correlation coefficient that can be computed, for example, according to the following equation:

$$C(j) = \frac{\sum_{i=1}^{N}[(TD(i)-\mu_T) \times (PD(i-j)-\mu_P)]}{N-1}, \quad (1)$$

where N is the number of heart-beat periods under consideration, j is an integer expressing a time-lag of the pacing data PD with respect to the timing data TD in heart-beat periods, and $$\mu_T = \frac{\sum_{i=1}^{N} TD(i)}{N}, \mu_P = \frac{\sum_{i=1}^{N} PD(i)}{N}. \quad (2)$$

The above-presented correlation coefficient C(j) can be used as the indicator of cardiac malfunction and abnormality. In light of empirical data, a positive value of the correlation coefficient C(j=1) means an increased probability of atrial fibrillation and a negative value of the correlation indicates a normal situation.

Figure 2B:
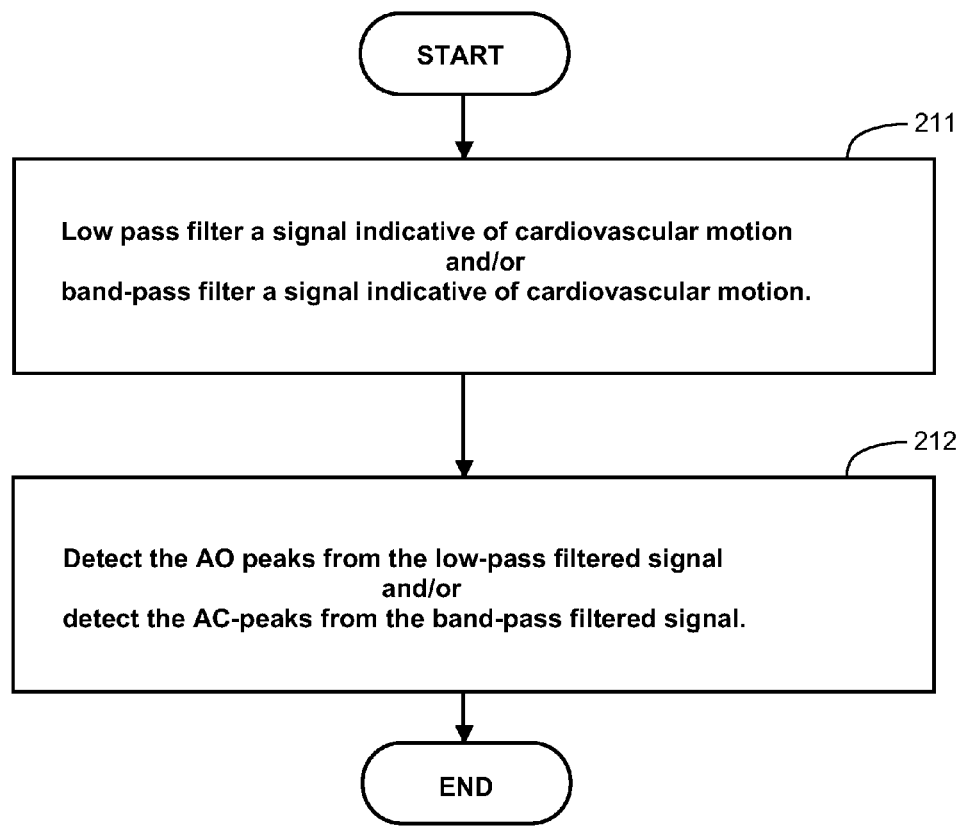
FIG. 2b illustrates a flow chart of a method according to an exemplifying embodiment of the invention for extracting AO data and/or AC data from a signal indicative of the cardiovascular motion.

FIG. 2b illustrates a flow chart of a method according to an exemplifying embodiment of the invention for extracting AO data and/or AC data from a signal indicative of the cardiovascular motion. The signal indicative of the cardiovascular motion is advantageously measured with an accelerometer in the "through chest"-direction that is typically referred to as the z-direction. The method comprises the following actions:
- action 211: low-pass filtering the signal indicative of the cardiovascular motion and/or band-pass filtering the signal indicative of the cardiovascular motion, and
- action 212: detecting the AO-peaks from the low-pass filtered signal and/or detecting the AC-peaks from the band-pass filtered signal.

The upper limit frequency of the low-pass filtering can be, for example but not necessarily, 30 Hz, and the pass-band of the band-pass filtering can be, for example but not necessarily, from 40 Hz up to 100 Hz. The low-pass filtering and/or the pass-band filtering facilitate the detection of the AO- and/or AC-peaks. The detected AO- and/or AC-peaks can be utilized when extracting for example the above-mentioned second wave pattern from the signal indicative of cardiovascular motion. The detected AO- and/or AC-peaks can be used for many other purposes too, e.g. for detecting an amplitude variation, a time variation, the heart-beat rate, the systolic intervals, and/or the diastolic intervals.

A method according to an exemplifying embodiment of the invention comprises detecting temporal lengths of AC-AO intervals and computing a time variation quantity indicative of strength of variation of the detected temporal lengths of the AC-AO intervals, where each of the AC-AO intervals is a time interval from one of the AC-peaks to the following one of the AO-peaks and the time variation quantity is indicative of cardiac malfunction and abnormality. This time variation quantity can be used together with the above-mentioned correlation between the timing data and the pacing data in order to increase reliability of the detection of possible cardiac malfunction and abnormalities. However, this time variation quantity can be used also alone.

A method according to an exemplifying embodiment of the invention comprises detecting temporal lengths of AC-AO intervals and temporal lengths of AO-AO intervals and computing a first ratio quantity indicative of the ratio between the temporal length of the AC-AO interval and the temporal length of the AO-AO interval within a same heart-beat period. Each of the AC-AO intervals is a time interval from one of the AC-peaks to the following one of the AO-peaks, each of the AO-AO intervals is a time interval from one of the AO-peaks to the following one of the AO-peaks, and the first ratio quantity is indicative of cardiac malfunction and abnormality. This first ratio quantity can be used together with the above-mentioned correlation between the timing data and the pacing data in order to increase reliability of the detection of possible cardiac malfunction and abnormalities. However, this first ratio quantity can be used also alone.

A method according to an exemplifying embodiment of the invention comprises detecting temporal lengths of AC-R intervals and temporal lengths of R-R intervals and computing a second ratio quantity indicative of a ratio between the temporal length of the AC-R interval and the temporal length of the R-R interval within a same heart-beat period. Each of the AC-R intervals is a time interval from one of the AC-peaks to the following one of the R-peaks, each of the R-R intervals is a time interval from one of the R-peaks to the following one of the R-peaks, and the second ratio quantity is indicative of cardiac malfunction and abnormality. This second ratio quantity can be used together with the above-mentioned correlation between the timing data and the pacing data in order to increase reliability of the detection of possible cardiac malfunction and abnormalities. However, this second ratio quantity can be used also alone.

Figure 5:
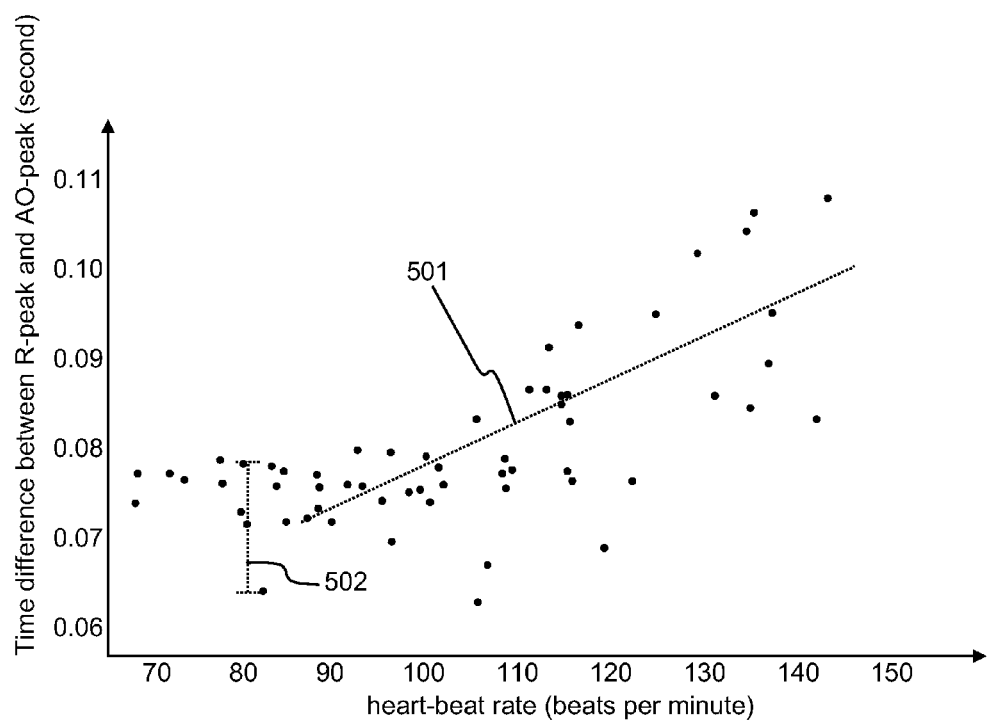
FIG. 5 shows time differences between the R-peak of an ECG waveform and the aortic valve opening "AO"-peak of a waveform indicative of cardiovascular motion at different heart-beat rates in an exemplifying case of atrial fibrillation.

FIG. 5 shows empirical values of the timing data obtained at different heart-beat rates in an exemplifying case of atrial fibrillation. Each black dot in FIG. 5 represents a) the time difference between the R-peak of an ECG waveform and the aortic valve opening "AO"-peak of a waveform indicative of cardiovascular motion in a certain heart-beat period and b) the heart-beat rate in the previous heart-beat period. The positive slope of the dashed line 501 shown in FIG. 5 illustrates the positive correlation between the timing data and the pacing data. As can be seen from FIG. 5, the trend of the timing data is increasing together with the heart-beat rate when the heart-beat rate is above about 85 beats per minute. In a normal case, the trend would be substantially constant or decreasing.

A method according to an exemplifying embodiment of the invention comprises producing a signal expressing atrial fibrillation in response to a situation in which the correlation coefficient C(j=1) is greater than a threshold. A suitable value for the threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds where each threshold represents a specific probability of atrial fibrillation or some other cardiac malfunction and/or abnormality. In some cases the threshold can be zero.

For another example, the pacing data for the heart-beat periods "i−1", "i", and "i+1" can be defined as PD(i−1)=HB(i−1), PD(i)=HB(i), and PD(i+1)=HB(i+1), respectively. In this case, a negative value of the correlation coefficient C(j=1) means an increased probability of atrial fibrillation and a positive value of the correlation indicates a normal situation. A method according to an exemplifying embodiment of the invention comprises producing a signal expressing atrial fibrillation in response to a situation in which the correlation coefficient C(j=1) is less than a threshold that can be, in some cases, zero.

In a method according to an exemplifying embodiment of the invention, the action 204 shown in FIG. 2a comprises determining variation of the timing data when the heart-beat rate is substantially constant. In light of empirical data, the degree of the variation is indicative of cardiac malfunction and abnormality. In FIG. 5, the range of the variation at the heart-beat rate 80 beats per minute is illustrated with the vertical dashed line segment 502. When the timing data indicates the time intervals between the R-peaks and the AO-peaks as illustrated in FIGS. 3a and 3b, the timing data represents the pre-ejection periods "PEP". It has been noticed that, during atrial fibrillation, there is stochastic variation in the PEP between successive heart-beat periods.

The degree of the above-mentioned variation can be expressed with the aid of a mathematical variation-quantity that can be computed, for example, according to the following equation:

$$V = \frac{\sqrt{\frac{\sum_{i=1}^{M}(TD(i)-\mu_T)^2}{M-1}}}{\mu_T} \times 100\%, \quad (3)$$

where V is the variation quantity, M is the number of timing data values under consideration at the heart-beat rate under consideration, and $$\mu_T = \frac{\sum_{i=1}^{M} TD(i)}{M}. \quad (4)$$

In light of empirical data, the variation-quantity V can be about 10% during atrial fibrillation and about 1-2% in a normal case.

A method according to an exemplifying embodiment of the invention comprises producing a signal expressing atrial fibrillation in response to a situation in which the variation-quantity V is greater than a threshold. A suitable value for the threshold can be determined on the basis of empirical data gathered from a group of patients and/or other persons. The threshold is not necessary a constant but the threshold can be changing according to the individual under consideration, according to time, and/or according to some other factors. It is also possible to construct a series of thresholds where each threshold represents a specific probability of atrial fibrillation or some other cardiac malfunction and/or abnormality.

A method according to an exemplifying embodiment of the invention comprises detecting the variation of the timing data at more than one heart-beat rate and using the detection results for determining the indicator of cardiac malfunction and abnormality. For example, the equations (3) and (4) can be used for obtaining the variation-quantities at several heart-beat rates and the final variation quantity can be formed with a mathematic-logical operation, e.g. the arithmetic average, from the variations-quantities related to the heart-beat rates under consideration.

Each peak value, e.g. the height of a single AO-peak, can be taken as a single point by searching a local maximum. Alternatively, the peak value can be obtained so that many samples are taken first from a time-window covering the peak under consideration and then the peak value is computed as a mathematical function, e.g. an arithmetic mean, of the samples in order to mitigate the effect of noise. The time window can be e.g. 100 ms, and the number of samples within the time window can be e.g. ten or more. The method based on the time-window is an example of digital filtering. Generally, there are numerous digital and analogue signal processing methods that can be used for mitigating the effect of noise in signals indicative of cardiovascular motion and in signals indicative of electromagnetic phenomena related to cardiac activity.

A method according to an exemplifying embodiment of the invention comprises optionally measuring the first signal indicative of electromagnetic phenomena related to cardiac activity and the second signal indicative of cardiovascular motion with sensor elements from individual's body. A method according to another exemplifying embodiment of the invention comprises reading these signals from a memory, in which case the signals have been measured earlier and recorded to the memory. A method according to an exemplifying embodiment of the invention comprises receiving the signals from an external data transfer system. Hence, the measuring is not an essential and necessary step of methods according to embodiments of the invention.

FIG. 4 illustrates a schematic illustration of an apparatus according to an exemplifying embodiment of the invention for determining information indicative of cardiac malfunctions and abnormalities. The apparatus comprises a signal interface 401 for receiving a first signal indicative of electromagnetic phenomena related to cardiac activity and a second signal indicative of cardiovascular motion. The apparatus comprises a processing device 402 coupled to the signal interface. The processing device is configured to

- extract from the first signal a first wave pattern repeating on a heart-beat rate and from the second signal a second wave pattern repeating on the heart-beat rate,
- form timing data, each timing value of which being indicative of a time period from a reference point of the first wave pattern belonging to one heart-beat period to a reference point of the second wave pattern belonging to the same heart-beat period, and
- determine correlation between the timing data and pacing data indicative of the heart-beat rate, the correlation being indicative of cardiac malfunction and abnormality.

The first signal may represent, for example, an electrocardiograph "ECG" waveform or an inductively measured waveform.

In an apparatus according to an exemplifying embodiment of the invention, the processing device 402 is configured to extract the R-peak from an ECG waveform and the AO-peak from a waveform indicative of cardiovascular motion. In this case, the R-peak represents the first wave pattern repeating on the heart-beat rate on the first signal and the AO-peak represents the second wave pattern repeating on the heart-beat rate on the second signal. The top of the R-peak can be the reference point of the first wave pattern and the top of the AO-peak can be the reference point of the second wave pattern.

In an apparatus according to another exemplifying embodiment of the invention, the processing device 402 is configured to extract the R-peak from an ECG waveform and the J-peak from a waveform indicative of cardiovascular motion. In this case, the R-peak represents the first wave pattern repeating on the heart-beat rate on the first signal and the J-peak represents the second wave pattern repeating on the heart-beat rate on the second signal. The top of the R-peak can be the reference point of the first wave pattern and the top of the J-peak can be the reference point of the second wave pattern.

In an apparatus according to an exemplifying embodiment of the invention, the processing device 402 is configured to extract the R-peak from an ECG waveform and the valley between the MC-peak and the AO-peak from a waveform indicative of cardiovascular motion. In this case, the R-peak represents the first wave pattern repeating on the heart-beat rate on the first signal and the valley between the MC-peak and the AO-peak represents the second wave pattern repeating on the heart-beat rate on the second signal. The top of the R-peak can be the reference point of the first wave pattern and the deepest point of the valley can be the reference point of the second wave pattern.

In an apparatus according to an exemplifying embodiment of the invention, the processing device 402 is configured to compute a correlation coefficient indicative of the degree of the correlation between the timing data and the pacing data:

$$C(j)=E\{(TD-\mu_T) \times (PD-\mu_P)\},$$

where $C(j)$ is the correlation coefficient, E is the expected value operator, TD is the timing data, $\mu_T$ is the mean of the timing data, PD is the pacing data, $\mu_P$ is the mean of the pacing data, and j is an integer expressing a time-lag of the pacing data with respect to the timing data in heart-beat periods.

Furthermore, the processing device 402 can be configured to compare the computed correlation coefficient $C(j)$ with one or more thresholds and to produce a signal expressing cardiac malfunction and abnormality in response to the situation in which the result of the comparison indicates presence of cardiac malfunction and abnormality. The signal can be, for example, a message shown on a display screen 406. The one or more thresholds are preferably adjustable parameters that can be supplied to the apparatus via its user interface.

In an apparatus according to an exemplifying embodiment of the invention, the processing device 402 is configured to detect time periods between successive R-peaks on the first signal. The detected time periods are indicative of the heart-beat rate as being inversely proportional to the heart-beat rate. Therefore, the detected time periods can be used as the pacing data or the pacing data can be constructed with the aid of the detected time periods.

In an apparatus according to an exemplifying embodiment of the invention, the processing device 402 is configured to form the pacing data so that each value of the pacing data represents an instantaneous value of the heart-beat rate, and produce a signal expressing atrial fibrillation in response to a situation in which the correlation coefficient is greater than a pre-determined threshold, e.g. zero.

In an apparatus according to an exemplifying embodiment of the invention, the processing device 402 is configured to form the pacing data so that each value of the pacing data represents a temporal length of one heart-beat period, and produce a signal expressing atrial fibrillation in response to a situation in which the correlation coefficient is less than a pre-determined threshold, e.g. zero.

In an apparatus according to an exemplifying embodiment of the invention, the processing device 402 is configured to determine variation of the timing data corresponding to a substantially constant heart-beat rate. The processing device can be configured to determine a variation-quantity indicative of the degree of the variation:

$$V = \frac{\sqrt{E\{(TD-\mu_T)^2\}}}{\mu_T},$$

where V is the variation-quantity, E is the expected value operator, TD is the timing data, and $\mu_T$ is the mean of the timing data at the heart-beat rate under consideration.

Furthermore, the processing device 402 can be configured to compare the computed variation-quantity V with one or more thresholds and to produce a signal expressing cardiac malfunction and abnormality in response to the situation in which the result of the comparison indicates presence of cardiac malfunction and abnormality. The signal can be, for example, a message shown on a display screen 406. The one or more thresholds are preferably adjustable parameters that can be supplied to the apparatus via its user interface.

In an apparatus according to an exemplifying embodiment of the invention, the processing device 402 is configured to detect the variation of the timing data at more than one heart-beat rate and to determine the indicator of cardiac malfunction and abnormality on the basis of the variations related to the more than one heart-beat rate. For example, the equations (3) and (4) can be used for obtaining the variation-quantities at several heart-beat rates and the final variation quantity can be formed with a mathematic-logical operation, e.g. the arithmetic average, from the variations-quantities related to the heart-beat rates under consideration.

An apparatus according to an exemplifying embodiment of the invention further comprises a first sensor element 403 for measuring the first signal from individual's body 409 and a second sensor element 404 for measuring the second signal from the individual's body. The first and second sensor elements are connected to the signal interface via one or more data transfer links each of which can be, for example, a radio link or a corded link. The data transfer from the sensor elements 403 and 404 to the signal interface 401 may take place either directly or via a data transfer network 405 such as e.g. a telecommunications network. In the exemplifying case shown in FIG. 4, both of the sensor elements 403 and 404 are connected to a radio transmitter 408. It is also possible that the apparatus comprising the processing device 406 is integrated with the sensor elements. In this case, the signal interface is actually a simple wiring from the sensor elements 403 and 404 to the processing device 402.

In this exemplifying case, the first sensor element 403 comprises electrodes suitable for being attached to individual's body. The first sensor element may further comprise, for example, an amplifier, a signal filter, and/or an analog-to-digital "AD" converter. The second sensor element 404 may comprise, for example, an accelerometer, a piezo-electronic sensor, an inclinometer, a pressure sensor, or any other element suitable for measuring force, acceleration, displacement, or any other physical quantity related to and indicative of cardiovascular motion. The second sensor element may further comprise, for example, an amplifier, a signal filter, and/or an analog-to-digital "AD" converter. An accelerometer is advantageously a three-axis accelerometer which is capable of measuring movements independently in three mutually orthogonal directions x, y, and z of e.g. the coordinate system 450 shown in FIG. 4. In this case, the second signal indicative of cardiovascular motion comprises three components and the second signal can be, for example, pre-processed by forming its Euclidian norm, i.e. the absolute value of the three component vector indicative of cardiovascular motion.

An apparatus according to an exemplifying embodiment of the invention is configured to record the first and second signals within a time window having a fixed temporal start point and a fixed temporal end point or within a sliding time window having a fixed temporal length and moving along with elapsing time. The apparatus may comprise an internal memory 407 for recording the signal and/or the apparatus may comprise a data port for connecting to an external memory.

An apparatus according to an exemplifying embodiment of the invention comprises means for pre-processing the first signal indicative of electromagnetic phenomena related to cardiac activity and/or the second signal indicative of cardiovascular motion. The pre-processing may comprise, for example, cancellation of noise on the second signal caused by e.g. breathing, non-cardiovascular movements of an individual, tremble caused by external reasons, etc. The means for pre-processing can be, for example, implemented with the processing device 402 or there can be one or more separate processing devices for the pre-processing.

In an apparatus according to an exemplifying embodiment of the invention, the processing device 402 is configured to low-pass filter the second signal indicative of the cardiovascular motion and to detect the above-mentioned AO-peaks from the low-pass filtered signal. A functional block 420 shown in FIG. 4 represents of the low-pass filtering, and a functional block 422 represents the detection of the AO-peaks.

In an apparatus according to an exemplifying embodiment of the invention, the processing device 402 is configured to band-pass filter the second signal indicative of the cardiovascular motion and to detect AC-peaks from the band-pass filtered signal, the AC-peaks being caused by the closures of the aortic valve. A functional block 421 shown in FIG. 4 represents of the band-pass filtering, and the functional block 422 represents the detecting the AC-peaks. In the exemplifying case illustrated in FIG. 4, there are both the low-pass filtering and the band-pass filtering and the functional block 422 represents the detection of both the AO- and AC-peaks. The upper limit frequency of the low-pass filtering can be, for example but not necessarily, 30 Hz, and the pass-band of the band-pass filtering can be, for example but not necessarily, from 40 Hz up to 100 Hz. The low-pass filtering and/or the pass-band filtering facilitate the detection of the AO- and/or AC-peaks. The detected AO- and/or AC-peaks can be utilized when extracting for example the above-mentioned second wave pattern from the signal indicative of cardiovascular motion. The detected AO- and/or AC-peaks can be used for many other purposes too, e.g. for detecting an amplitude variation, a time variation, the heart-beat rate, the systolic intervals, and/or the diastolic intervals.

In an apparatus according to an exemplifying embodiment of the invention, the processing device 502 is configured to detect temporal lengths of AC-AO intervals and to compute a time variation quantity indicative of strength of variation of the detected temporal lengths of the AC-AO intervals. Each of the AC-AO intervals is a time interval from one of the AC-peaks to the following one of the AO-peaks and the time variation quantity is indicative of cardiac malfunction and abnormality. This time variation quantity can be used together with the above-mentioned correlation between the timing data and the pacing data in order to increase reliability of the detection of possible cardiac malfunction and abnormalities. However, this time variation quantity can be used also alone.

In an apparatus according to an exemplifying embodiment of the invention, the processing device 502 is configured to detect temporal lengths of AC-AO intervals and temporal lengths of AO-AO intervals and to compute a first ratio quantity indicative of the ratio between the temporal length of the AC-AO interval and the temporal length of the AO-AO interval within a same heart-beat periods. Each of the AC-AO intervals is a time interval from one of the AC-peaks to the following one of the AO-peaks, each of the AO-AO intervals is a time interval from one of the AO-peaks to the following one of the AO-peaks, and the first ratio quantity is indicative of cardiac malfunction and abnormality. This first ratio quantity can be used together with the above-mentioned correlation between the timing data and the pacing data in order to increase reliability of the detection of possible cardiac malfunction and abnormalities. However, this first ratio quantity can be used also alone.

In an apparatus according to an exemplifying embodiment of the invention, the processing device 502 is configured to configured to detect temporal lengths of AC-R intervals and temporal lengths of R-R intervals and to compute a second ratio quantity indicative of a ratio between the temporal length of the AC-R interval and the temporal length of the R-R interval within a same heart-beat period. Each of the AC-R intervals is a time interval from one of the AC-peaks to the following one of the R-peaks, each of the R-R intervals is a time interval from one of the R-peaks to the following one of the R-peaks, and the second ratio quantity is indicative of cardiac malfunction and abnormality. This second ratio quantity can be used together with the above-mentioned correlation between the timing data and the pacing data in order to increase reliability of the detection of possible cardiac malfunction and abnormalities. However, this second ratio quantity can be used also alone.

The processing device 402 can be, for example, implemented with one or more processor circuits, each of which can be a programmable processor circuit provided with appropriate software, a dedicated hardware processor such as, for example, an application specific integrated circuit "ASIC", or a configurable hardware processor such as, for example, a field programmable gate array "FPGA".

A computer program according to an exemplifying embodiment of the invention comprises software modules for determining information indicative of cardiac malfunctions and abnormalities. The software modules comprise computer executable instructions for controlling a programmable processor to:

extract, from a first signal indicative of electromagnetic phenomena related to cardiac activity, a first wave pattern repeating on a heart-beat rate, extract, from a second signal indicative of cardiovascular motion, a second wave pattern repeating on the heart-beat rate, form timing data, each timing value of which being indicative of a time period from a reference point of the first wave pattern belonging to one heart-beat period to a reference point of the second wave pattern belonging to the same heart-beat period, and determine correlation between the timing data and pacing data indicative of the heart-beat rate, the correlation being indicative of cardiac malfunction and abnormality.

In a computer program according to an exemplifying embodiment of the invention, the software modules comprise at least one of the following:

computer executable instructions for controlling a programmable processor to low-pass filter a signal indicative of the cardiovascular motion and to detect the AO-peaks from the low-pass filtered signal, and/or computer executable instructions for controlling a programmable processor to band-pass filter the signal indicative of the cardiovascular motion and to detect the AC-peaks from the band-pass filtered signal.

The software modules can be e.g. subroutines or functions implemented with a suitable programming language and with a compiler suitable for the programming language and the programmable processor.

A computer program product according to an exemplifying embodiment of the invention comprises a computer readable medium, e.g. a compact disc "CD", encoded with a computer program according to an embodiment of invention.

A signal according to an exemplifying embodiment of the invention is encoded to carry information defining a computer program according to an embodiment of invention.

The specific examples provided in the description given above should not be construed as limiting the scope and/or the applicability of the appended claims. Furthermore, it is also to be noted that, in many cases, the present invention can be used together with other techniques for detecting cardiac malfunctions and abnormalities.

What is claimed is:

1. An apparatus comprising:
a signal interface for receiving a first signal indicative of electromagnetic cardiac activity and a second signal indicative of cardiovascular motion, and
a processing device coupled to the signal interface,
the processing device being arranged and configured to:
extract from the first signal a first wave pattern repeating on a heart-beat rate and from the second signal a second wave pattern repeating on the heart-beat rate,
form timing data, each timing value of which being indicative of a time period from a reference point of the first wave pattern belonging to one heart-beat period to a reference point of the second wave pattern belonging to the same heart-beat period,
determine a correlation between the timing data and pacing data indicative of the heart-beat rate,
produce, on the basis of the correlation, a third signal indicative of cardiac malfunction and abnormality, and
make the third signal available to a user external to the processing device,
wherein the processing device is configured to compute a correlation coefficient indicative of the degree of the correlation between the timing data and the pacing data:

$$C(j)=E\{(TD-\mu_T)\times(PD-\mu_P)\},$$

where C(j) is the correlation coefficient, E is the expected value operator, TD is the timing data, $\mu_T$ is the mean of the timing data, PD is the pacing data, $\mu_P$ is the mean of the pacing data, and j is an integer expressing a time-lag of the pacing data with respect to the timing data in heart-beat periods.

2. The apparatus according to claim 1, wherein the apparatus further comprises a first sensor element for measuring the first signal and a second sensor element for measuring the second signal.

3. The apparatus according to claim 2, wherein the second sensor element comprises one of the following: an accelerometer, a piezo-electronic sensor, an inclinometer, a pressure sensor.

4. The apparatus according to claim 1, wherein the processing device is configured to extract from the first signal the R-peak and from the second signal the AO-peak, the R-peak being caused by depolarization of the ventricular muscle tissue and representing the first wave pattern repeating on the heart-beat rate on the first signal, and the AO-peak being caused by opening of the aortic valve and representing the second wave pattern repeating on the heart-beat rate on the second signal.

5. The apparatus according to claim 4, wherein the processing device is configured to use the top of the R-peak as the reference point of the first wave pattern and the top of the AO-peak, the top of the J-peak, or the deepest point of the valley between the MC-peak and the AO-peak as the reference point of the second wave pattern.

6. The apparatus according to claim 4, wherein the processing device is configured to low-pass filter the second signal indicative of the cardiovascular motion and to detect the AO-peak from the low-pass filtered signal.

7. The apparatus according to claim 6, wherein an upper limit frequency of the low-pass filtering is 30 Hz.

8. The apparatus according to claim 4, wherein the processing device is configured to band-pass filter the second signal indicative of the cardiovascular motion and to detect AC-peaks from the band-pass filtered signal, the AC-peaks being caused by closures of the aortic valve.

9. The apparatus according to claim 8, wherein a pass-band of the band-pass filtering is from 40 Hz to 100 Hz.

10. The apparatus according to claim 8, wherein the processing device is configured to detect temporal lengths of AC-AO intervals and to compute a time variation quantity indicative of strength of variation of the detected temporal lengths of the AC-AO intervals, each of the AC-AO intervals being a time interval from one of the AC-peaks to the following one of the AO-peaks and the time variation quantity being indicative of cardiac malfunction and abnormality.

11. The apparatus according to claim 8, wherein the processing device is configured to detect temporal lengths of AC-AO intervals and temporal lengths of AO-AO intervals and to compute a first ratio quantity indicative of a ratio between the temporal length of the AC-AO interval and the temporal length of the AO-AO interval within a same heart-beat period, each of the AC-AO intervals being a time interval from one of the AC-peaks to the following one of the AO-peaks, each of the AO-AO intervals being a time interval from one of the AO-peaks to the following one of the AO-peaks, and the first ratio quantity being indicative of cardiac malfunction and abnormality.

12. The apparatus according to claim 8, wherein the processing device is configured to configured to detect temporal lengths of AC-R intervals and temporal lengths of R-R intervals and to compute a second ratio quantity indicative of a ratio between the temporal length of the AC-R interval and the temporal length of the R-R interval within a same heart-beat period, each of the AC-R intervals being a time interval from one of the AC-peaks to the following one of the R-peaks, each of the R-R intervals being a time interval from one of the R-peaks to the following one of the R-peaks, and the second ratio quantity being indicative of cardiac malfunction and abnormality.

13. The apparatus according to claim 1, wherein the processing device is configured to determine variation of the timing data corresponding to a substantially constant heart-beat rate, the degree of the variation being indicative of cardiac malfunction and abnormality.

14. The apparatus according to claim 13, wherein the processing device is configured to determine a variation-quantity indicative of the degree of the variation of the timing data:

$$V = \frac{\sqrt{E\{(TD - \mu_T)^2\}}}{\mu_T},$$

where V is the variation-quantity, E is the expected value operator, TD is the timing data, and $\mu_T$ is the mean of the timing data at the heart-beat rate under consideration.

15. The apparatus according to claim 1, wherein the processing device is configured to detect time periods between successive R-peaks on the first signal in order to obtain the pacing data, the detected time periods being indicative of the heart-beat rate as being inversely proportional to the heart-beat rate.

16. The apparatus according to claim 1, wherein the processing device is configured to form the pacing data so that each value of the pacing data represents an instantaneous value of the heart-beat rate, and produce a signal expressing atrial fibrillation in response to a situation in which the correlation coefficient is greater than a threshold.

17. The apparatus according to claim 16, wherein the processing device is configured to use zero as the threshold.

18. A method comprising a processing device performing the steps of:
extracting, from a first signal indicative of electromagnetic cardiac activity, a first wave pattern repeating on a heart-beat rate, and extracting, from a second signal indicative of cardiovascular motion, a second wave pattern repeating on the heart-beat rate,
forming timing data, each timing value of which being indicative of a time period from a reference point of the first wave pattern belonging to one heart-beat period to a reference point of the second wave pattern belonging to the same heart-beat period, determining a correlation between the timing data and pacing
data indicative of the heart-beat rate,
producing, on the basis of the correlation, a third signal indicative of cardiac malfunction and abnormality,
making the third signal available to a user external to the processing device, and
computing a correlation coefficient indicative of the degree of the correlation between the timing data and the pacing data:

$$C(j) = E\{(TD - \mu_T) \times (PD - \mu_P)\},$$

where C(j) is the correlation coefficient, E is the expected value operator, TD is the timing data, $\mu_T$ is the mean of the timing data, PD is the pacing data, $\mu_P$ is the mean of the pacing data, and j is an integer expressing a time-lag of the pacing data with respect to the timing data in heart-beat periods.

19. The method according to claim 18, wherein the method comprises extracting from the first signal the R-peak and from the second signal the AO-peak, the R-peak being caused by depolarization of the ventricular muscle tissue and representing the first wave pattern repeating on the heart-beat rate on the first signal, and the AO-peak being caused by opening of the aortic valve and representing the second wave pattern repeating on the heart-beat rate on the second signal.

20. The method according to claim 19, wherein the top of the R-peak is the reference point of the first wave pattern and the top of the AO-peak, the top of the J-peak, or the deepest point of the valley between the MC-peak and the AO-peak is the reference point of the second wave pattern.

21. The method according to claim 19, wherein the method comprises low-pass filtering the second signal indicative of the cardiovascular motion and detecting the AO-peak from the low-pass filtered signal.

22. The method according to claim 21, wherein an upper limit frequency of the low-pass filtering is 30 Hz.

23. The method according to claim 19, wherein the method comprises band-pass filtering (211) the second signal indicative of the cardiovascular motion and detecting (212) AC-peaks from the band-pass filtered signal, the AC-peaks being caused by closures of the aortic valve.

24. The method according to claim 23, wherein a passband of the band-pass filtering is from 40 Hz to 100 Hz.

25. The method according to claim 23, wherein the method comprises detecting temporal lengths of AC-AO intervals and computing a time variation quantity indicative of strength of variation of the detected temporal lengths of the AC-AO intervals, each of the AC-AO intervals being a time interval from one of the AC-peaks to the following one of the AO-peaks and the time variation quantity being indicative of cardiac malfunction and abnormality.

26. The method according to claim 23, wherein the method comprises detecting temporal lengths of AC-AO intervals and temporal lengths of AO-AO intervals and computing a first ratio quantity indicative of a ratio between the temporal length of the AC-AO interval and the temporal length of the AO-AO interval within a same heart-beat period, each of the AC-AO intervals being a time interval from one of the AC-peaks to the following one of the AO-peaks, each of the AO-AO intervals being a time interval from one of the AO-peaks to the following one of the AO-peaks, and the first ratio quantity being indicative of cardiac malfunction and abnormality.

27. The method according to claim 23, wherein the method comprises detecting temporal lengths of AC-R intervals and temporal lengths of R-R intervals and computing a second ratio quantity indicative of a ratio between the temporal length of the AC-R interval and the temporal length of the R-R interval within a same heart-beat period, each of the AC-R intervals being a time interval from one of the AC-peaks to the following one of the R-peaks, each of the R-R intervals being a time interval from one of the R-peaks to the following one of the R-peaks, and the second ratio quantity being indicative of cardiac malfunction and abnormality.

28. The method according to claim 18, wherein the determining (204) of the indicator of cardiac malfunction and abnormality comprises determining variation of the timing data corresponding to a substantially constant heart-beat rate, the degree of the variation being indicative of cardiac malfunction and abnormality.

29. The method according to claim 28, wherein a variation-quantity indicative of the degree of the variation of the timing data is computed:

$$V = \frac{\sqrt{E\{(TD - \mu_T)^2\}}}{\mu_T},$$

where V is the variation-quantity, E is the expected value operator, TD is the timing data, and $\mu_T$ is the mean of the timing data at the heart-beat rate under consideration.

30. The method according to claim 18, wherein the method comprises detecting time periods between successive R-peaks on the first signal in order to obtain the pacing data, the detected time periods being indicative of the heart-beat rate as being inversely proportional to the heart-beat rate.

31. The method according to claim 18, wherein each value of the pacing data represents an instantaneous value of the heart-beat rate and the method comprises producing a signal expressing atrial fibrillation in response to a situation in which the correlation coefficient is greater than a threshold.

32. The method according to claim 31, wherein the threshold is zero.

33. A non-transitory computer readable medium encoded with a computer program comprising computer executable instructions for causing a programmable processor to:

extract, from a first signal indicative of electromagnetic cardiac activity, a first wave pattern repeating on a heart-beat rate, extract, from a second signal indicative of cardiovascular motion, a second wave pattern repeating on the heart-beat rate, form timing data, each timing value of which being indicative of a time period from a reference point of the first wave pattern belonging to one heart-beat period to a reference point of the second wave pattern belonging to the same heart-beat period, determine correlation between the timing data and pacing data indicative of the heart-beat rate, produce, on the basis of the correlation, a third signal indicative of cardiac malfunction and abnormality, make the third signal available to a user external to the programmable processor, and compute a correlation coefficient indicative of the degree of the correlation between the timing data and the pacing data:

$$C(j) = E\{(TD - \mu_T) \times (PD - \mu_P)\},$$

where C(j) is the correlation coefficient, E is the expected value operator, TD is the timing data, $\mu_T$ is the mean of the timing data, PD is the pacing data, $\mu_P$ is the mean of the pacing data, and j is an integer expressing a time-lag of the pacing data with respect to the timing data in heart-beat periods.

\* \* \* \* \*

UNITED STATES PATENT AND TRADEMARK OFFICE
CERTIFICATE OF CORRECTION

PATENT NO. : 9,585,580 B2
APPLICATION NO. : 14/396204
DATED : March 7, 2017
INVENTOR(S) : Juhani Airaksinen et al.

It is certified that error appears in the above-identified patent and that said Letters Patent is hereby corrected as shown below:

On the Title Page

Left Column:
"(73) Assignee: TURUN YLIOPISTO, Turun Yliopisto (FI)"

Should be replaced with:
--(73) Assignee: PRECORDIOR OY, Turku (FI)--.

Signed and Sealed this
Twenty-eighth Day of May, 2019

Andrei Iancu
*Director of the United States Patent and Trademark Office*